(12) United States Patent
Bacher et al.

(10) Patent No.: US 7,056,304 B2
(45) Date of Patent: Jun. 6, 2006

(54) MEDICAL INSTRUMENT

(75) Inventors: Uwe Bacher, Tuttlingen (DE); Horst Dittrich, Immendingen (DE); Martin Oberlaender, Tuttingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 10/372,690

(22) Filed: Feb. 24, 2003

(65) Prior Publication Data
US 2003/0167040 A1 Sep. 4, 2003

Related U.S. Application Data

(63) Continuation of application No. PCT/EP02/08143, filed on Jul. 22, 2002.

(30) Foreign Application Priority Data
Jul. 24, 2001 (DE) .............................. 101 35 979

(51) Int. Cl.
*A61M 5/178* (2006.01)
(52) U.S. Cl. .............................. 604/167.03; 604/164.02
(58) Field of Classification Search ........... 604/167.04, 604/167.03, 256, 264, 167.01, 167.02, 164.02, 604/246, 164.01, 167.06; 606/167, 170, 606/185
See application file for complete search history.

(56) References Cited

U.S. PATENT DOCUMENTS 4,931,042 A * 6/1990 Holmes et al. ........ 604/164.12
5,397,314 A * 3/1995 Farley et al. ................ 604/256
6,066,117 A * 5/2000 Fox et al. .................... 604/249
6,077,249 A * 6/2000 Dittrich et al. ........ 604/167.03
6,159,182 A * 12/2000 Davis et al. ........... 604/167.06

FOREIGN PATENT DOCUMENTS

| DE | G 89 16 160 | 7/1994 |
|---|---|---|
| DE | G 94 18 005 | 2/1995 |
| DE | 39 23 243 C2 | 12/1995 |
| DE | 297 00 762 | 7/1998 |
| DE | 196 19 065 C2 | 12/2000 |
| WO | WO 94/19052 | 9/1994 |

* cited by examiner

*Primary Examiner*—Nicholas D. Luchessi
*Assistant Examiner*—Matthew DeSanto
(74) *Attorney, Agent, or Firm*—St. Onge Steward Johnston & Reens LLC

(57) ABSTRACT

The invention relates to a medical instrument with a hollow instrument canal that is configured inside a housing and can be closed by means of at least one valve body and rotated into open position by means of an instrument inserted into the instrument canal. The at least one valve body is configured as a flap consisting of an essentially non-bendable material mounted on the housing so that it can be rotated by means of an elastic, bendable connecting element configured as a wire spring in such a way that the valve body is pre-tensioned in the closed direction. A medical instrument with a valve body of simple construction, which insulates reliably, is distinguished according to the invention in that the connecting element on the one hand is secured on the housing and on the other hand carries the valve body, so that the connecting element can be secured in a ring groove configured in the housing.

28 Claims, 11 Drawing Sheets

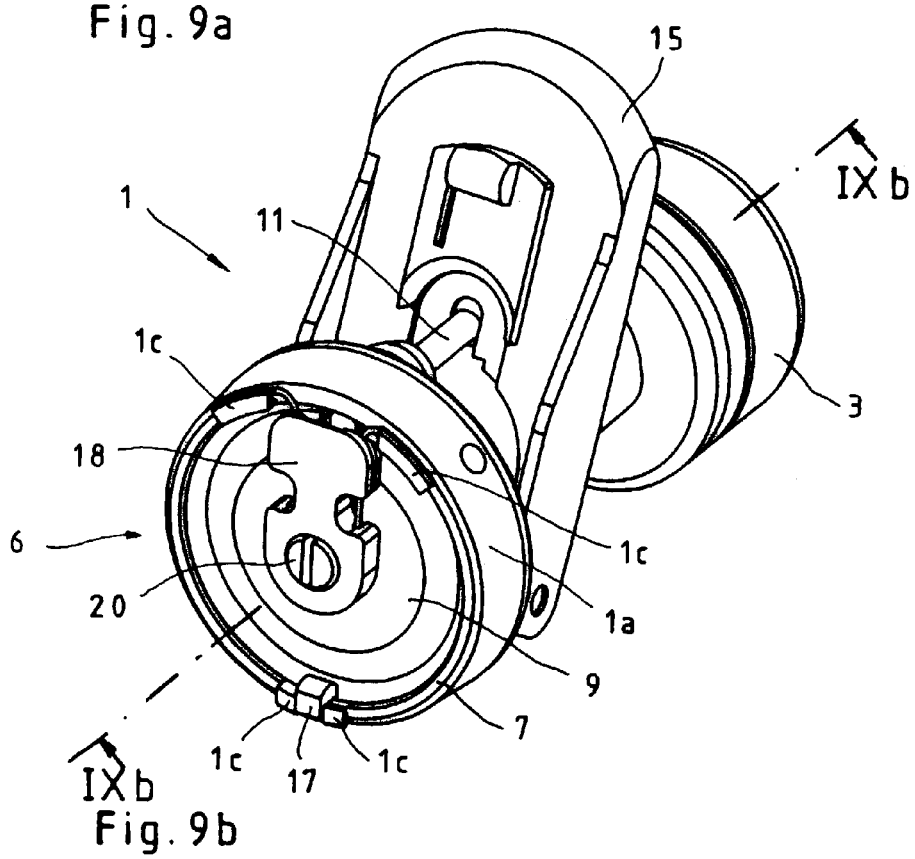
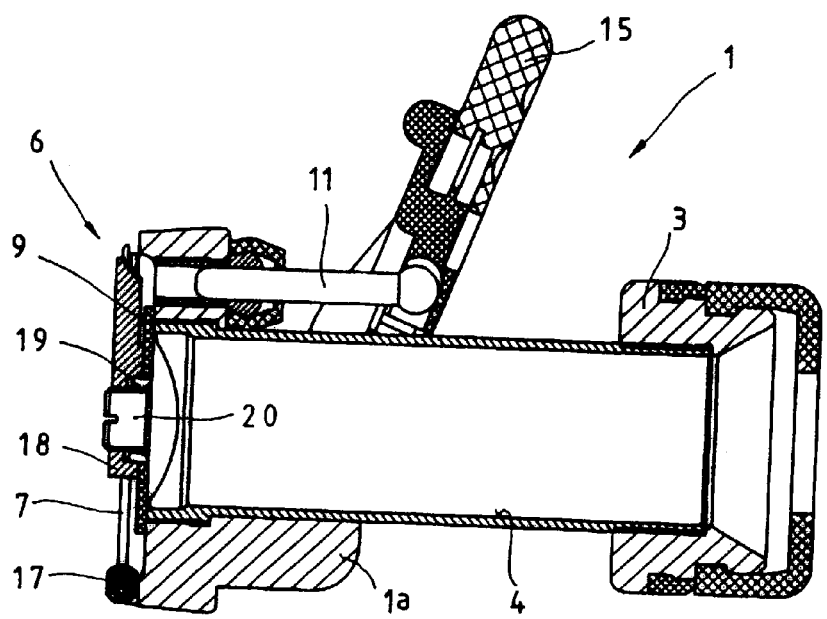

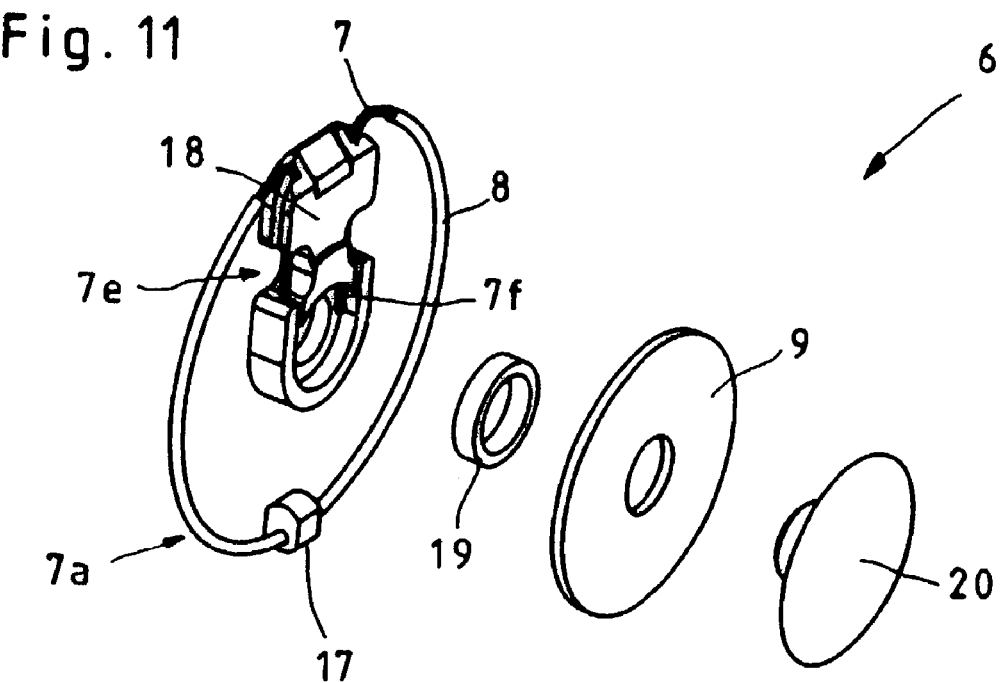

MEDICAL INSTRUMENT

This application is a continuation of pending International Patent Application No. PCT/EP02/08143 filed on Jul. 22, 2002, which designates the United States and claims priority of pending German Application No. 101 35 979, filed on Jul. 24, 2001.

FIELD OF THE INVENTION

The invention relates to a medical instrument with a hollow instrument canal that is configured inside a housing and can be closed by means of at least one valve body and rotated into open position by means of an instrument inserted into the instrument canal. The at least one valve body is configured as a flap consisting of an essentially non-bendable material mounted on the housing so that it can be rotated by means of an elastic, bendable connecting element configured as a wire spring in such a way that the valve body is pre-tensioned in the closed direction.

Medical instruments of this type are in use as trocars, for instance. Trocars serve as a means of introducing operating instruments for endoscopic operations, for instance, into a patient's abdominal cavity. For this purpose the trocar sheath is placed on the abdominal covering, a trocar pin is inserted into the hollow instrument canal, an aperture is made in the abdominal covering with the help of the trocar pin, and then the trocar sheath is introduced through the aperture into the abdominal area. The trocar pin can then be withdrawn again from the trocar sheath. Because it is common in endoscopic operations in the abdominal area to fill the abdominal area with gas in order to expand the operating area and form a pneumatic peritoneum, the hollow instrument canal of the trocar sheath can be closed by means of a valve body so that the gas cannot escape from the abdominal area by way of the trocar sheath as the instrument is being removed. The known valve bodies are configured in such a way that they are opened by means of an instrument inserted into the instrument canal and close again independently when the instrument is withdrawn.

A generic medical instrument configured, as a trocar sheath is known, for instance, from patent DE 297 00 762 U1. With this familiar trocar, the connecting element that pre-tensions the valve body is configured as a U-shaped arched wire spring. The free ends of the spring are arched inward at right angles at various spots and secured in the housing in drilled openings at intervals to one another. Because of the various stud lengths of the spring, rotation of the valve body causes tensioning of the spring, so that the spring pressures the valve body in the direction toward closed position. The spacing of the drill holes for receiving the folded free ends of the spring make it essential that the free ends of the spring studs must be curved at precisely defined locations, since otherwise the spring is not secured to the housing. Because of the strict adherence to narrow allowable values, production of the springs is labor intensive and thus costly. In addition, because of the varying stud lengths, the spring can be secured to the housing only in one position, making the installation of this known trocar difficult.

An addition medical instrument configured as a trocar sheath with a valve body mounted in the instrument canal is known from DE-C1-43 06 205. With this known medical instrument, the valve body is configured as a flap constructed of silicon, which is connected with a carrier piece that can be rotated by means of a film hinge, where the carrier piece in turn can be secured to the housing in such a way that the valve body can close the instrument canal and, by inserting an instrument, can be released again. This known valve body can be produced economically as a die-cast part and in addition is easily removable for cleaning and replacement purposes; nevertheless the known construction has the disadvantages that, on one hand, the slippery silicon flap does not insulate sufficiently, since the film hinge causes only slight pre-tensioning of the valve body in closed position, and on the other hand, there is the risk that the film hinge can break down, especially from eccentric activation of the closed valve flap.

Another medical instrument configured as a trocar with a valve body for closing a hollow instrument canal is known from DE-C2-39 23 243. With this known construction, the valve flap consists of a non-bendable material and can be manually opened by means of a push rod, so that upon introducing a sharp instrument into the instrument canal the point of the instrument is not damaged when the valve flap is pushed open and so that, when pieces of tissue are removed by the valve flap, the tissue sample is not damaged, or is not abraded by the gripping clamp. This known construction, however, is so complex that the valve flap cannot be removed by the user for purposes of cleaning or replacement.

On the basis of this state of the art, the aim of this invention is to design a medical instrument of the aforementioned type in such a way that it can be constructed simply and economically that the reliably insulating valve body in particular can be easily removed for cleaning purposes or for replacement.

The invention fulfills this aim in that the connecting element on the one hand is secured on the housing and on the other hand carries the valve body, so that the connecting element can be secured in a ring groove configured in the housing.

The mounting of the connecting element on the housing on the one hand, and the mounting of the valve body on the connecting element on the other, in a practical embodiment of the invention, is ensured by means of ring grooves on the housing and on the valve body, where the connecting element, preferably configured as a multiply bent wire spring, can be secured in the ring groove on the housing while the ring groove on the valve body serves to receive the connecting element.

The valve body configured as a flap is connected with the housing only by means of the elastic, bendable connecting element, so that it requires only dismantling of the connecting element with the valve body or else dismantling of the valve body from the connecting element, in order to be able to remove the valve body for cleaning or replacement purposes.

In a preferred embodiment of the invention, the ring groove is configured as an interrupted ring groove. The interruptions of the ring groove are configured as apertures in the ring groove in a radial direction in such a way that in the most extreme case the ring groove consists of only a few circle segments.

To ensure that the valve body is correctly positioned when secured on the housing when the ring groove for receiving the connecting element consists only of individual interrupted circle segments, at least one positioning element working in conjunction with at lest one ring groove segment is mounted on the connecting element.

The use of encircling ring groove for receiving the connecting element on the housing and on the valve body constitutes a means of securing the connecting element that is especially simple to produce and easy to install and dismantle, in which the practical workability of this type of medical instrument is clearly facilitated and improved.

The construction unit consisting of connecting element and valve body is economical to produce. The connecting element and the valve body are connected by airtight clamping. The valve body can therefore be constructed of at least two parts, which at least partly enclose a portion of the connecting element foreseen for this purpose, on the basis of their reciprocal linking to one another, for instance by means of pressuring, bolting, or cementing. Likewise, a single-unit valve body can be connected by means of cementing to the corresponding segment of the connecting element. In an additional embodiment of the invention, the corresponding portion of the connecting element can be caste into the valve body. Through this economical production method, the construction unit can be employed as a disposable component.

In an additional embodiment of the invention, the part of the connecting element that can be secured in the ring groove on the housing is surrounded by a tube of an inelastic material, so that the outer diameter of the connecting element is only slightly smaller than the inner diameter of the tub and the connecting element and the tube are sealed together. To produce this airtight connection, it is proposed in connection with this invention that both components should be firmly connected to one another by means of pressuring or soldering, especially laser soldering. Through the choice of the position of the pressure spots, the pre-tensioning and release force of the valve body can be adjusted exactly to the particular requirements.

Use of the connecting element installed in the tube is intended to prevent slippage of the connecting element placed in the ring groove when the valve body is swiveled.

The connecting element is preferably constructed of elastic material such as spring steel or super-elastic alloys such as Ni—Ti, Cu—Al—Ni or Cu—Zn—Al alloys. The selection of the material of the connecting element allows optimization of pre-tensioning and air-tightness. This pre-tensioning causes the valve body to place itself back on the valve seating automatically and with sufficient pressure after withdrawal of the instrument out of the instrument canal, in order to insulate the instrument canal reliably.

In an additional embodiment of the invention it is proposed that the connecting element should be of composite construction with at least two intertwined strands and the individual strands of the connecting element should be connected to one another at individual spots through pressuring or soldering. Use of wire consisting of several strands twisted together lends the connecting element the necessary elasticity to permit the swiveling out of the valve body on the one hand, and to ensure a firm, stable holding of the connecting element in the ring groove on the other hand.

The inventive valve body consists preferably of a hard plastic.

To improve the sealing off of the instrument canal by means of the valve body, it is proposed in keeping with this invention that an insulating ring, especially made of an elastomer plastic, should be securable on the valve body and an insulating surface coaxially surrounding the instrument canal should be configured on the housing to hold the insulating ring of the valve body. This insulating surface, in practical embodiments of the invention, should preferably be configured as a raised insulating rim or level surface. Likewise the insulating surface configured essentially parallel to the valve level can be bordered by a ridge, with the course of the ridge corresponding to the outer shape of the insulating ring in the axial direction. The insulating ring mounted on the valve body should preferably be designed to be replaceable, to facilitate cleaning on the one hand and economical solution of insulating problems by simple replacement of the insulating rings on the other hand.

To prevent sensitive points of instruments from being damaged by being forced to push the valve body into the instrument canal, and so that, when pieces of tissue are removed, a tissue sample is not damaged by the valve flap or is not abraded by the gripping clamp, it is further proposed with the invention that the valve body in addition should be mountable in the open position by means of a manually operable mechanism. By means of this mechanism, it is now possible, alternatively with the pushing of the valve body with the instrument inserted into the instrument canal, to open the valve body manually from outside in order to prevent contact of the points of the instrument and/or the tissue sample with the valve body.

In a practical embodiment of the invention, the manually operable mechanism is configured as a push rod arranged eccentrically, especially parallel, to the instrument canal, and this push rod can be pushed in the longitudinal direction of the instrument canal by means of an activating element mounted on the housing. Use of the inventive connecting element is especially advantageous in this configuration, because this connecting element has sufficient stability against the eccentric pressure from the push rod.

It is proposed, with an initial embodiment of the invention, that the activating element should be configured as a disc that can be pushed parallel to the instrument canal and that is pre-tensioned by means of a spring in the closed direction of the valve body. Pre-tensioning of the activating element in the closed direction of the valve body ensures that the activating element is kept in a rest position, in which the valve body is closed.

In a second embodiment of the invention, the activating element for driving the push rod is formed from a lever mounted on the housing so that it can be rotated, and the lever is advantageously pre-tensioned by means of a spring in the closed direction of the valve body.

The plane of the valve opening toward the longitudinal axis of the instrument canal can vary by wide margins and is preferably 90 degrees.

Finally, it is proposed with the invention that it should be possible to secure an additional component to the housing in such a manner that the additional component holds the ring groove or ring groove segments, at least partially enclosing the connecting element in the ring groove or ring groove segments, where the housing is advantageously a trocar head and the additional component is a trocar sheath of a trocar that can be secured on the trocar head.

BRIEF DESCRIPTION OF DRAWINGS

Additional characteristics and advantages of the invention can be seen from the following description of the related illustrations, which depict schematically and only in exemplary fashion four embodiments of an inventive medical instrument. The illustrations are as follows.

DETAILED DESCRIPTION OF DRAWINGS

Figure 1:
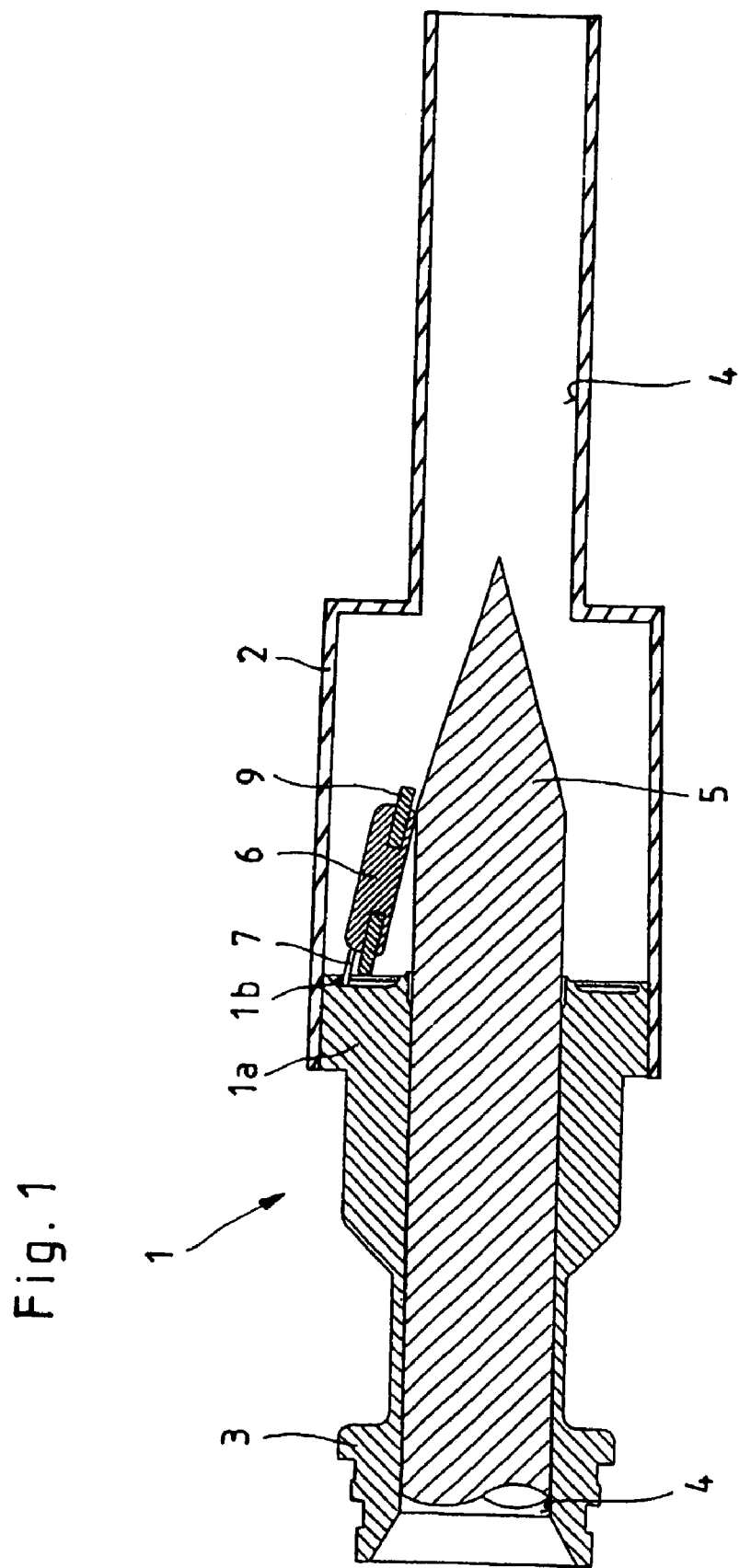
FIG. 1 Longitudinal section through a first embodiment of an inventive medical instrument configured as a trocar FIG. 2a Perspective view of the trocar head of the trocar according to FIG. 1 with trocar pin introduced into the instrument canal and with valve body rotated into open position FIG. 2b Perspective view corresponding to FIG. 2a but without trocar pin, and depicting the valve body in the closed position FIG. 3 Schematic longitudinal section along the cutting line III—III according to FIG. 2a FIG. 4 Schematic longitudinal section along the cutting line IV—IV according to FIG. 2b FIG. 5 Schematic perspective view of the connecting element with valve body secured to it in accordance with an initial inventive embodiment FIG. 6 Perspective view corresponding to FIG. 5 but depicting a second inventive embodiment of the connecting element FIG. 7 Schematic longitudinal section corresponding to FIG. 3 but depicting a second inventive embodiment FIG. 8 Schematic longitudinal section corresponding to FIG. 7 but depicting a third inventive embodiment FIG. 9a Schematic perspective view of a trocar head with closed valve body, depicting a fourth inventive embodiment of the connecting element FIG. 9b Schematic longitudinal section along the cutting line IX b—IX b in accordance with FIG. 9a FIG. 10a Perspective view corresponding to FIG. 9a but depicting the valve body in the open position FIG. 10b Schematic longitudinal section along the cutting line X b—X b in accordance with FIG. 10a FIG. 11 Explosive depiction of the valve body in accordance with FIGS. 9a to 10b

FIG. 1 shows in longitudinal section a trocar consisting of a trocar head 1 and a trocar housing 2. The trocar head 1 has a handle 3 on the proximal end and is crossed in the longitudinal direction by a centrally arranged hollow instrument canal 4, which continues in the trocar sheath 2.

FIGS. 2a and 2b show a perspective view in two different operating positions of the trocar head 1 of the trocar for introducing endoscopic operating instruments in accordance with FIG. 1.

Figure 2:
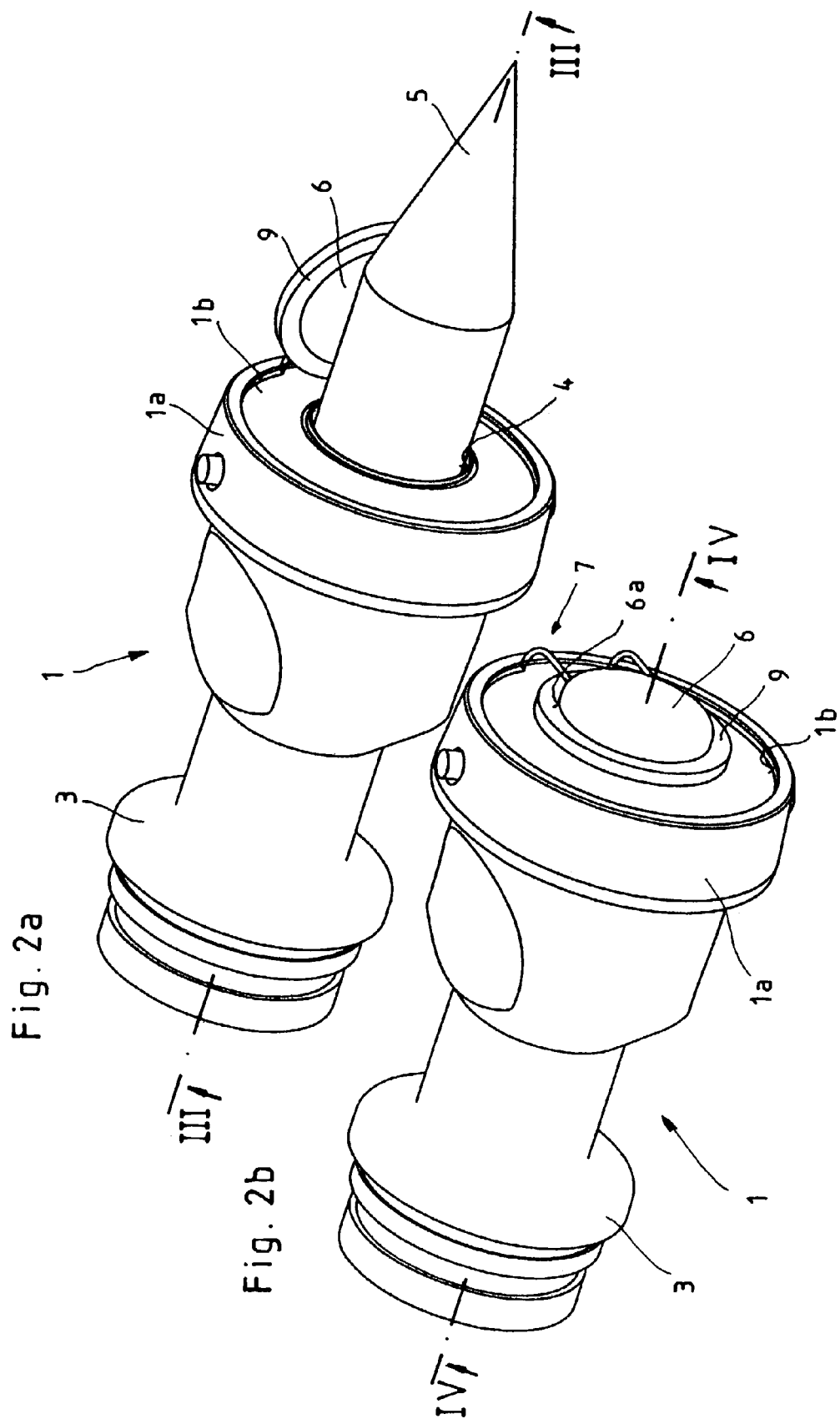
Figure 3:
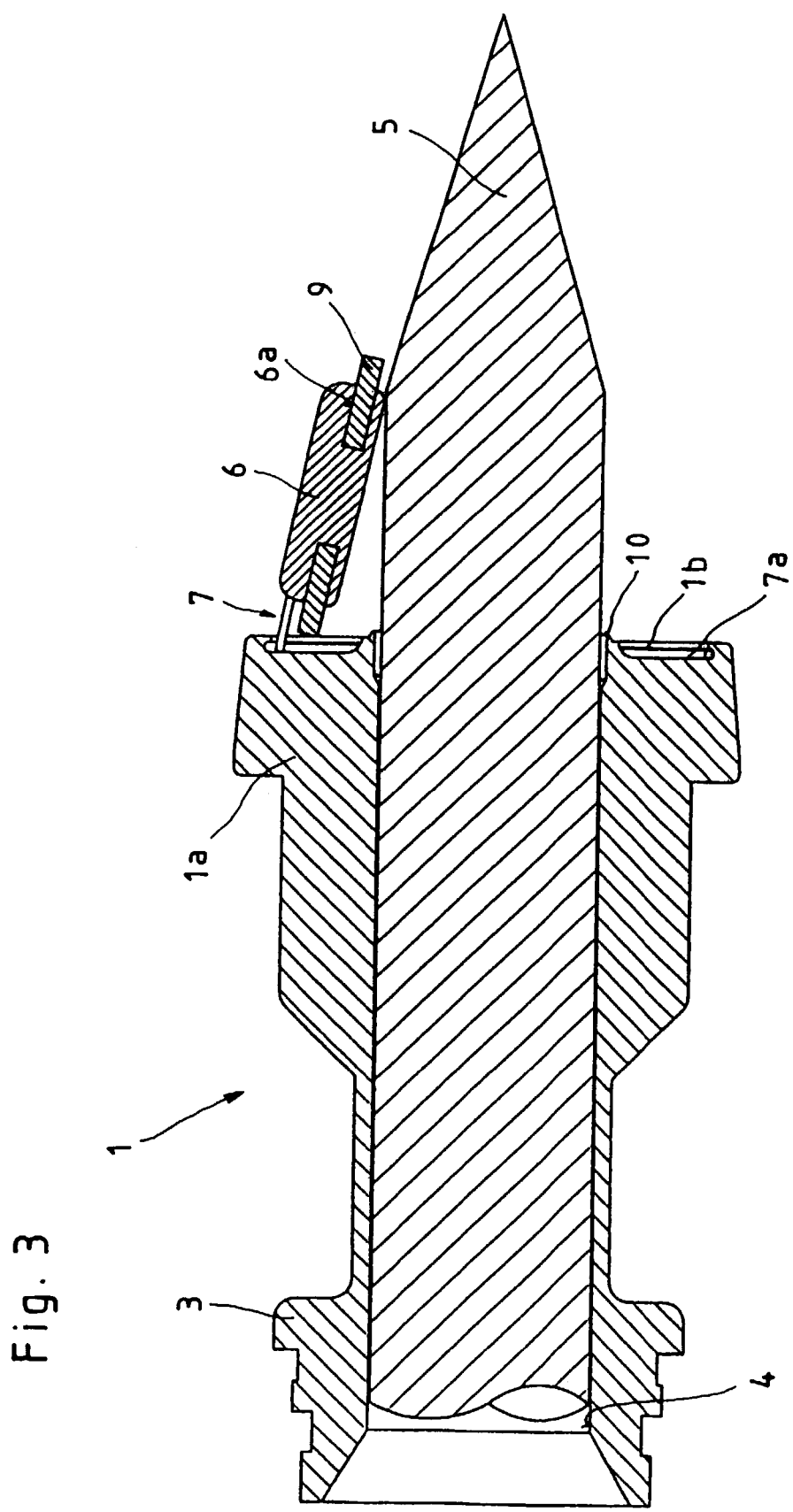

The hollow instrument canal 4 serves to receive a trocar pin 5 at the start of the operation, as shown in FIGS. 1, 2a, and 3, which pin creates an aperture, for instance in the patient's abdominal cover. The trocar sheath 2 is then inserted into this aperture and the trocar pin 5 is then withdrawn from the instrument canal 4. During the ensuing operation a whole range of endoscopic instruments can be introduced into the operating area by way of the instrument canal 4. Because it is customary in endoscopic operations of the abdominal area to fill the patient's abdominal area with gas in order to expand the operating area and to form a pneumatic peritoneum, the hollow instrument canal 4 of the trocar can be closed by means of a valve body 6 in order to prevent expulsion of gas during withdrawal of an instrument from the instrument canal 4.

The valve body 6 configured as a valve flap in the illustrated embodiments is mounted on the housing la of the trocar head 1 so that it can be rotated by way of an elastic, bendable connecting element 7 configured as a spring wire. The valve body 6 mounted on the housing la in such manner can be rotated between an open position (FIGS. 1, 2a, 3, 7, 8, and 10a) and a closed position (FIGS. 2b, 4, and 9a).

The ring groove 1b configured in the housing 1a serves to secure the connecting element 7 on the housing 1a of the trocar head 1. As can be seen in particular from the cross-sectional illustrations of FIGS. 1, 3, 4, 7, and 8, the connecting element 7 configured as a spring wire is secured in the ring groove 1b of the housing 1a that forms an overlap. In the embodiments shown in FIGS. 1 to 8, a ring groove 6a configured in the valve body 6 serves to secure the valve body 6 to the connecting element 7. The insertion of the connecting element 7 in the ring groove 6a of the valve body 6 is most clearly seen from the schematic illustrations of FIGS. 5 and 6.

Figure 4:
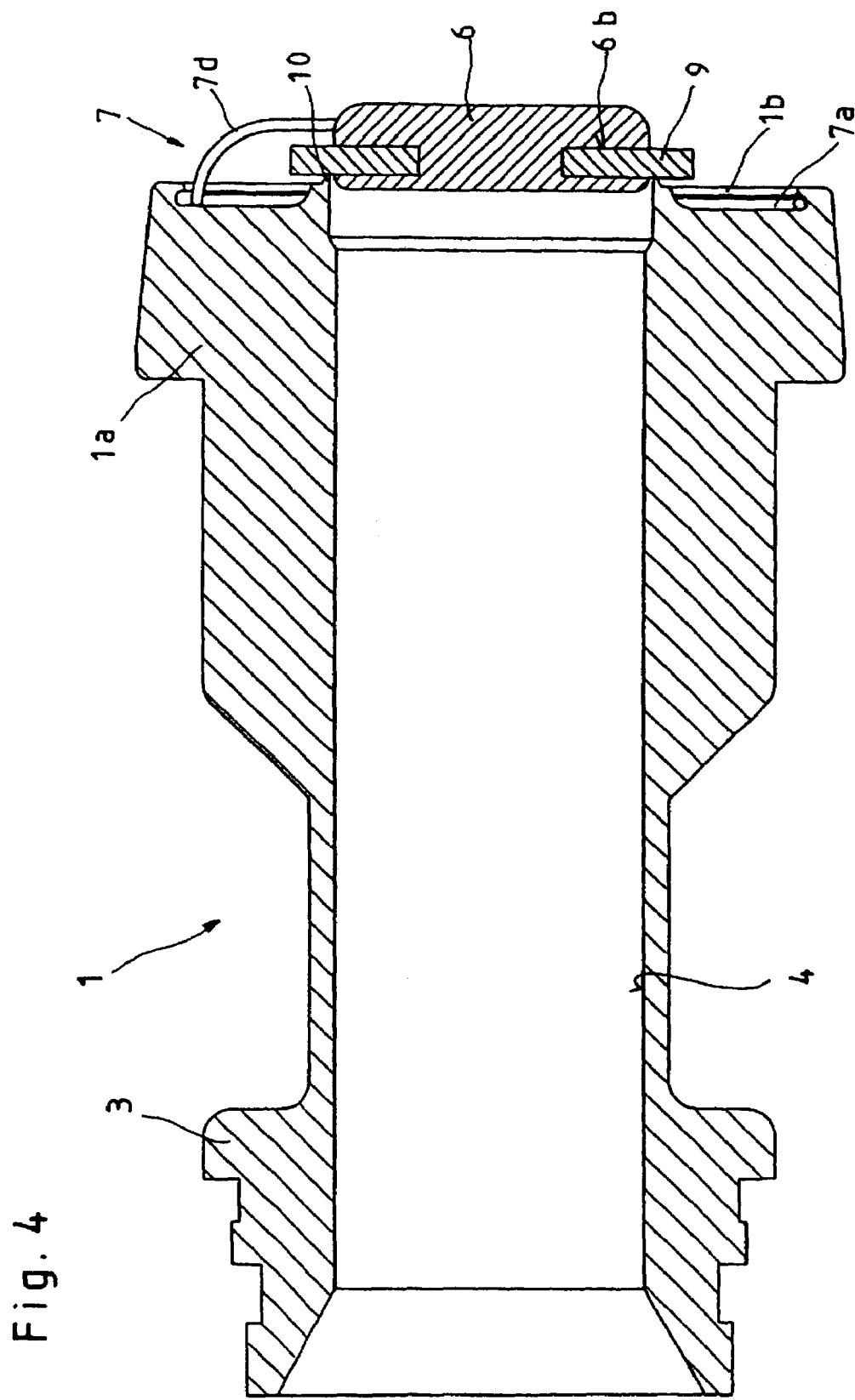

The shape of the connecting elements 7 of the illustrated embodiments in FIGS. 1 to 8 can best be seen by combining FIGS. 2b, 4, 5, and 6. In the first embodiment, shown in FIG. 5, part of the spring wire forming the combining element 7 is secured in the ring groove 1b of the housing 1a and consists of two semicircular segments 7a which are connected to one another by means of a section 7b that is basically arched outward at an upward right angle from the plane of the circle segment 7a. In order to form a loop 7c to fit into the ring groove 6a of the valve body 6, the section 7b has an arc-shaped curve 7d at about 90 degrees, so that the loop 7c, as can be seen in FIG. 4, is arranged parallel to the plane of the circle segments 7a in the closed position of the valve body. Because of the material rigidity of the multiply arched spring wire, the valve body 6 secured in the loop 7c is pre-tensioned in the closed direction. This pre-tensioning of the valve body 6 ensures that the valve body 6, after withdrawal of the instrument out of the instrument canal 4, automatically repositions itself to provide insulation before the aperture of the instrument canal 4. This pre-tensioning can be increased by reducing the angle between the segment 7b and the arc-shaped curvatures.

Figure 5:
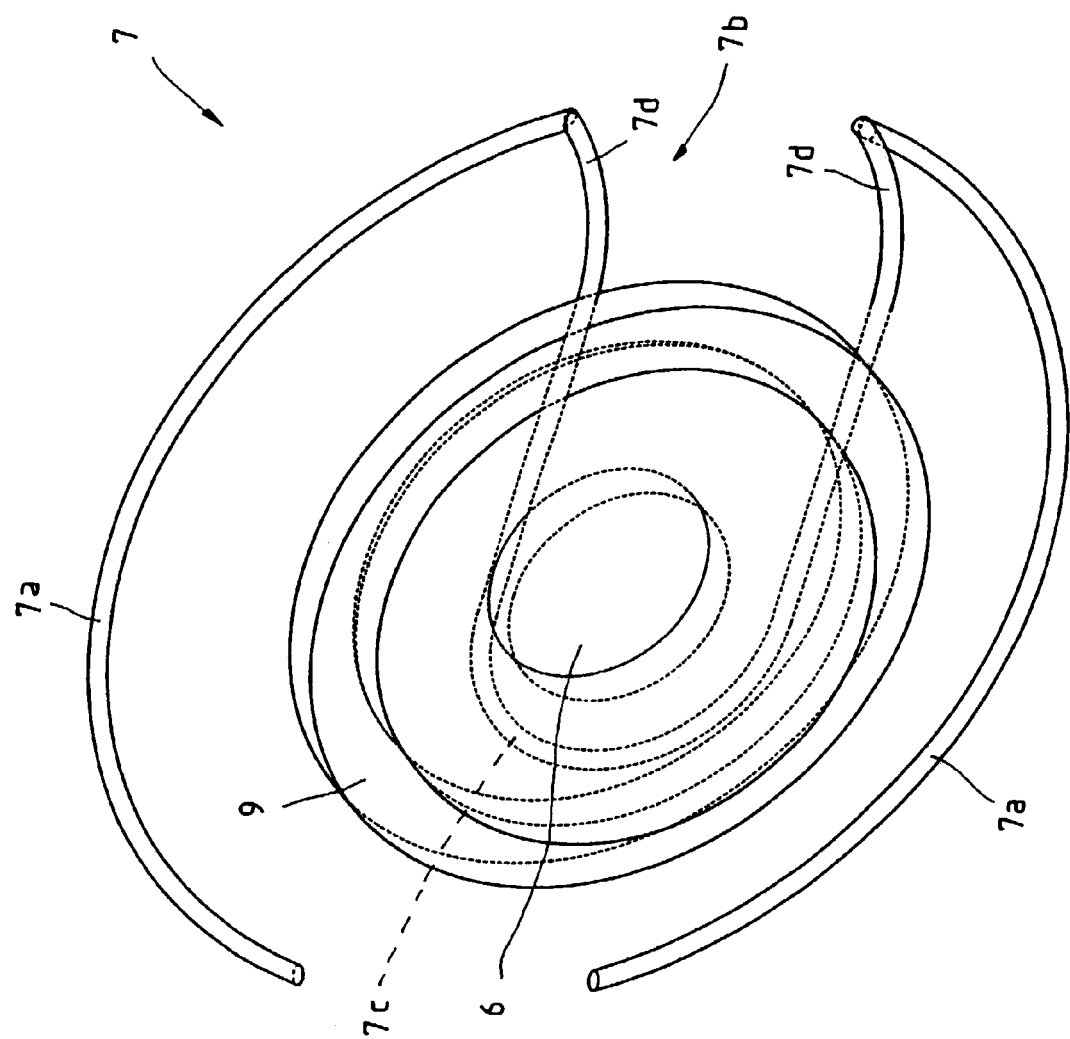
Figure 6:
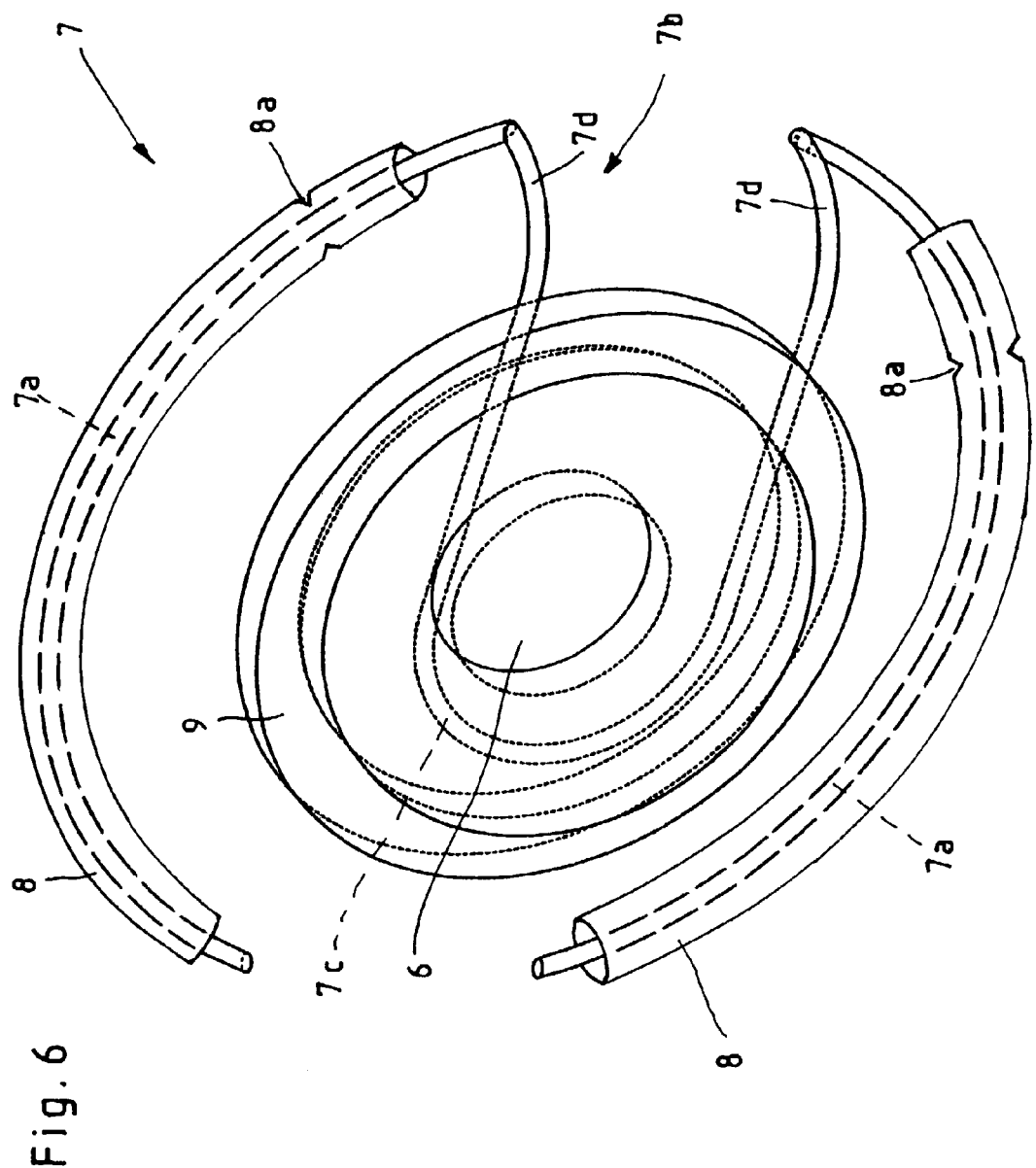
Figure 7:
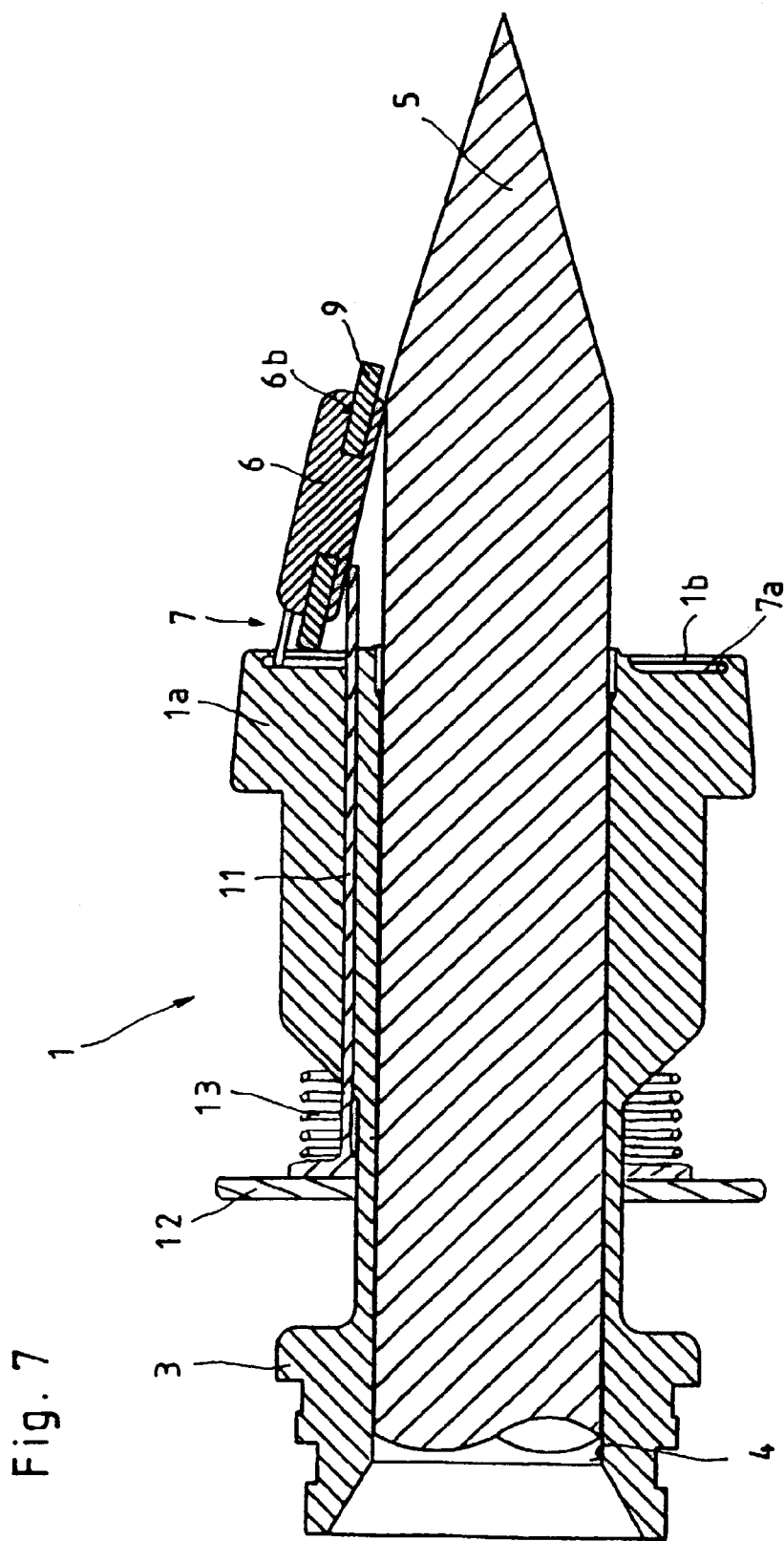

The second embodiment of the connecting element, illustrated in FIG. 6, is distinguished from the embodiment of FIG. 5 in that the circle segments 7a of the connecting element 7, which can be secured in the ring groove 1b of the housing 1a, are surrounded by tubes 8 of an inelastic material, and the tubes 8 are sealed together with the circle segments 7a of the connecting element 7. Thanks to the mounting of the connecting element 7 in the tube 8 and the selective sealing of the two components, it is simple for the connecting element 7 on the one hand to have sufficient flexibility to allow rotation of the valve body 6, and on the other hand for the connecting element 7 not to be able to slip inside the ring groove 1b when the wire is twisted from the rotation of the valve body 6.

In the illustrated case, the sealing is achieved through pressure. Through the selection and positioning of the pressure spots 8a, the pre-tensioning and the release force of the valve body 6 can be adjusted to the particular requirements.

As an alternative to pressuring the tube 8 and connecting element 7, the tube 8 and connecting element 7 can also be soldered together. Laser soldering is particularly appropriate here, because it allows soldering to be done with exactitude on predetermined locations. For this purpose, a hole extending to the connecting element 7 is bored in the tube 8 at the designated soldering points and the tube 8 is soldered with connecting element 7 in this bore hole.

To ensure a safe and reliably insulating positioning of the valve body 6 on the housing 1a surrounding the instrument canal 4, an insulating ring 9 on the one hand is installed in a second ring groove 6b on the valve body 6 in such a manner that it can be replaced, and on the other hand the housing 1a has an insulating surface, configured as a raised insulating rim 10, which coaxially surrounds the instrument canal 4, and on this insulating surface the valve body 6 holds the insulating ring 9, as is shown in FIG. 4.

In the first embodiment illustrated in FIGS. 1 to 4, the valve body 6 opens exclusively because an instrument is shoved through the instrument canal 4 and this instrument with its point strikes the valve body 6 and rotates it into the open position, as seen in FIGS. 1, 2a, and 3.

Because there is a risk, with instruments with especially sharp and/or sensitive points, that these points can become dulled by pressure against the valve body 6 or can even be damaged, and to ensure that upon removal of pieces of tissue by the valve flap the tissue sample is not damaged or is not abraded by the gripping clamp, it is possible in the embodiments shown in FIGS. 7 to 11 to open the valve body 6 by means of a manually activated mechanism. In the second embodiment of a trocar, in FIG. 7, this mechanism consists of a push rod 11 stored in the housing 1a eccentrically and parallel to the instrument canal 4, and this push rod 11 can be pushed in the longitudinal direction of the instrument canal 4 by means of an activating element stored in the housing a and configured as a disk 12. To avoid inadvertent opening of the valve body 6 by mans of the push rod 11, the disk 12 is pre-tensioned in the closed direction of the valve body 6 to activate the push rod 11 by means of a spring 13.

Figure 8:
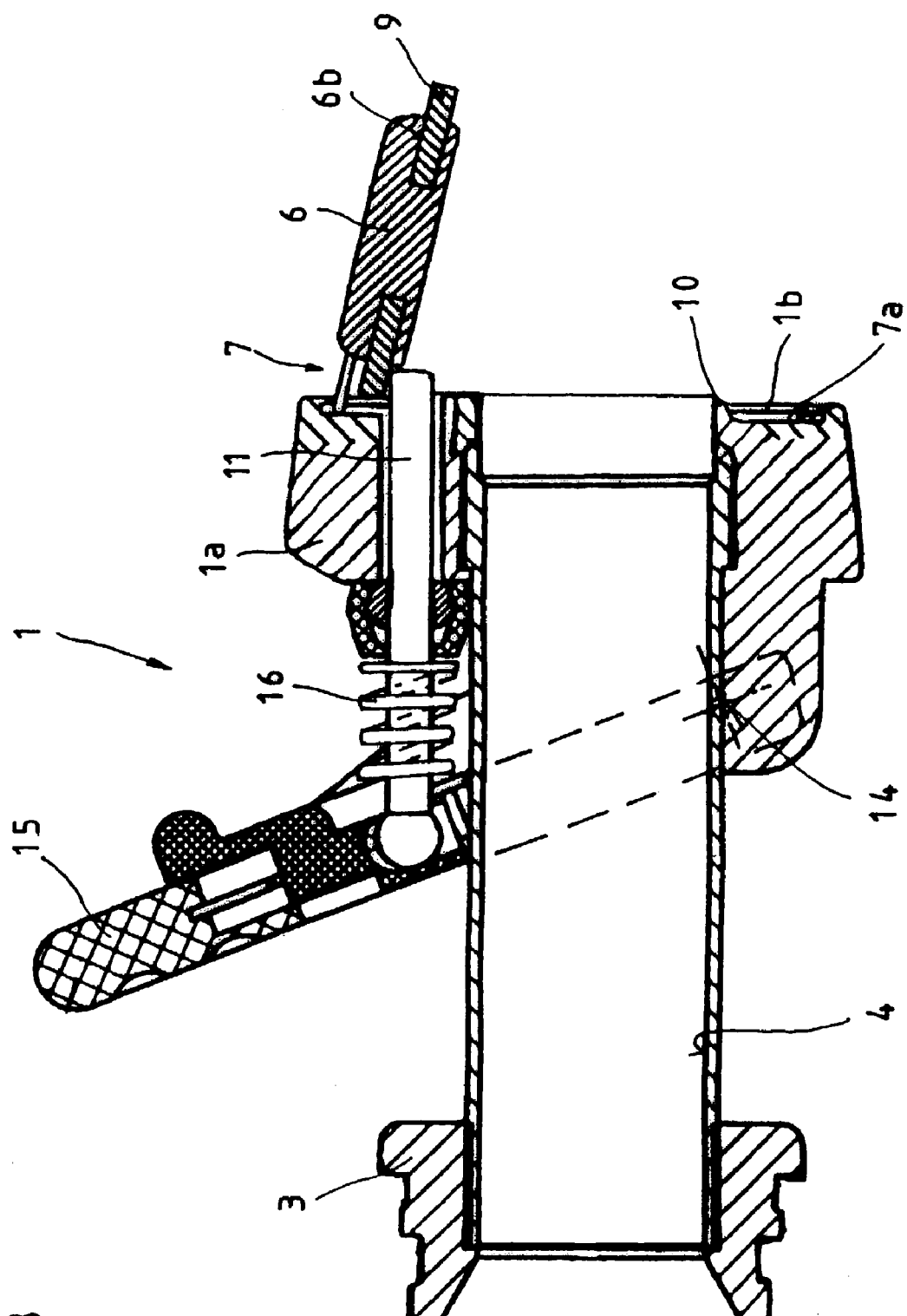

In the third embodiment as seen in FIG. 8, the activating element for pushing the push rod 11 is configured as a lever 15 mounted on the housing 1a which can be rotated around a turning point 14. This embodiment, as well, includes a spring 16 in order to pre-tension the lever 15 in the closed direction of the valve body 6.

In addition to the possibility, as shown, to connect the connecting element 7 with the valve body 6 by means of securing the loop 7c in the ring groove 6a of the valve body 6, it is also possible for the connecting element 7 to be cast in the material of the valve body 6 in order to produce an enduring link. Likewise the valve body 6 can be constructed of at least two parts, which after being joined to one another surround the loop 7c of the connecting element.

The fourth embodiment, as shown in FIGS. 9a to 11, is distinguished from the previously described embodiments essentially in that the ring groove 1b for receiving the connecting element 7 is configured, not as a continuous groove but instead as interrupted so that the ring groove 1b consists only of a few ring groove segments 1c representing circle segments. As can be seen from FIGS. 9b and 10b, the ring groove 1b in this embodiment consists of only four ring groove segments 1c.

As to be seen especially from FIG. 11, the part of the spring wire forming the connecting element 7, which is secured in the ring groove segments 1c of the housing 1a, consists of an almost completely closed circle segment 7a and a segment 73 arched radially inward, by means of which the ends 7f of the spring wire are secured to the valve body 6. In this embodiment as well, the connecting element 7 is partially mounted in a tube 8.

For the appropriate positioning of the connecting element 7 as well of the valve body 6 connected with the connecting element 7 on the housing 1a, at least one positioning element 17 is mounted on the connecting element 7 and works together with at least one ring groove segment 1c of the ring groove 1b. In the illustrated embodiment the connecting element 7 has a positioning element 17, which is arranged between two ring groove segments 1c in such a way that the connecting element 7 can no longer be pushed in this position relative to the housing 1a.

As to be seen from FIG. 1, the trocar sheath 2 can be secured on the housing 1a of the trocar head 1 in such a way that the trocar sheath 2 encloses the ring groove 1b or the ring groove segments 1c at least partly, in such a way that the connecting element 7 is held in the ring groove 1b or in the ring groove segments 1c and cannot slip out of the ring groove 1b or the ring groove segments 1c.

The valve body 6, which is to be secured on the connecting element 7, in this fourth embodiment, as seen in FIG. 11, is constructed in four parts and consists of an insulating mounting 18 that can be mounted on the ends 7f of the connecting element 7, a clamp segment 19, the insulating ring 9, and a bolt 20 by means of which the clamp segment 19 and the insulating ring 9 can be secured on the insulating mounting 18. Upon tightening of the bolt 20, the ends 7f of the connecting element 7 are clamped in the insulating mounting 18 in such a way that the valve body 6 is mounted securely on the connecting element 7.

Figure 10A:
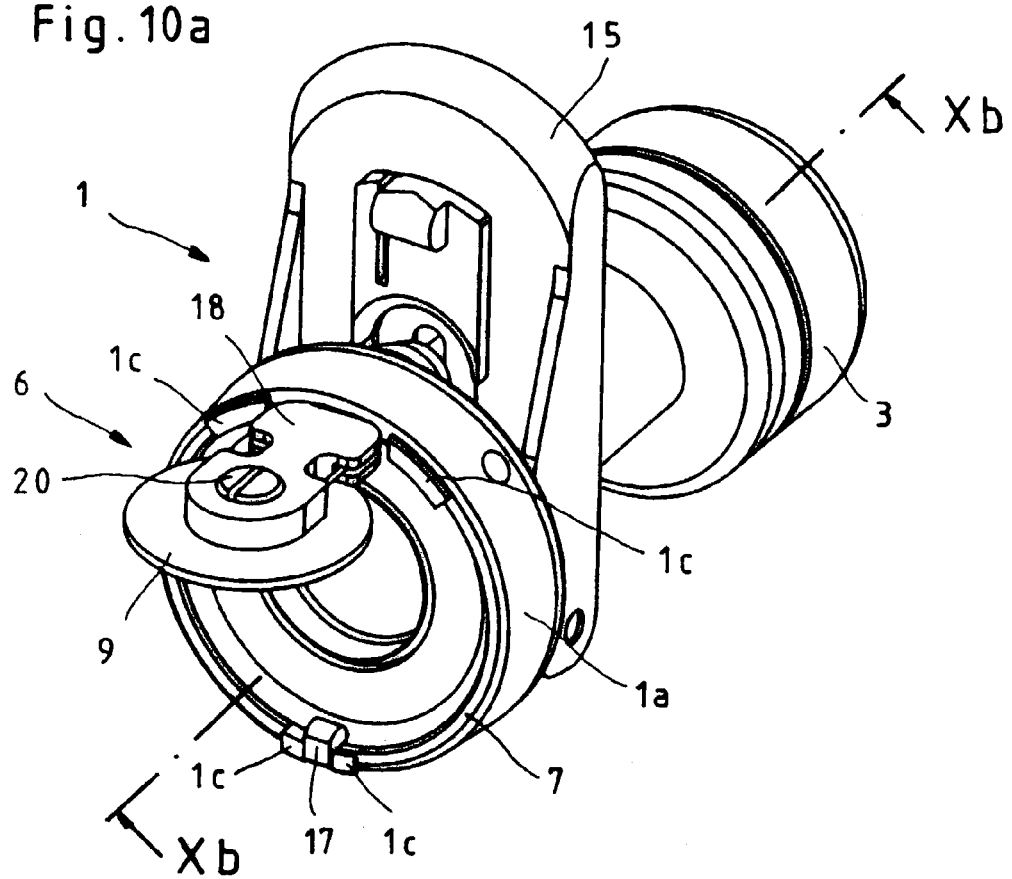
Figure 10B:
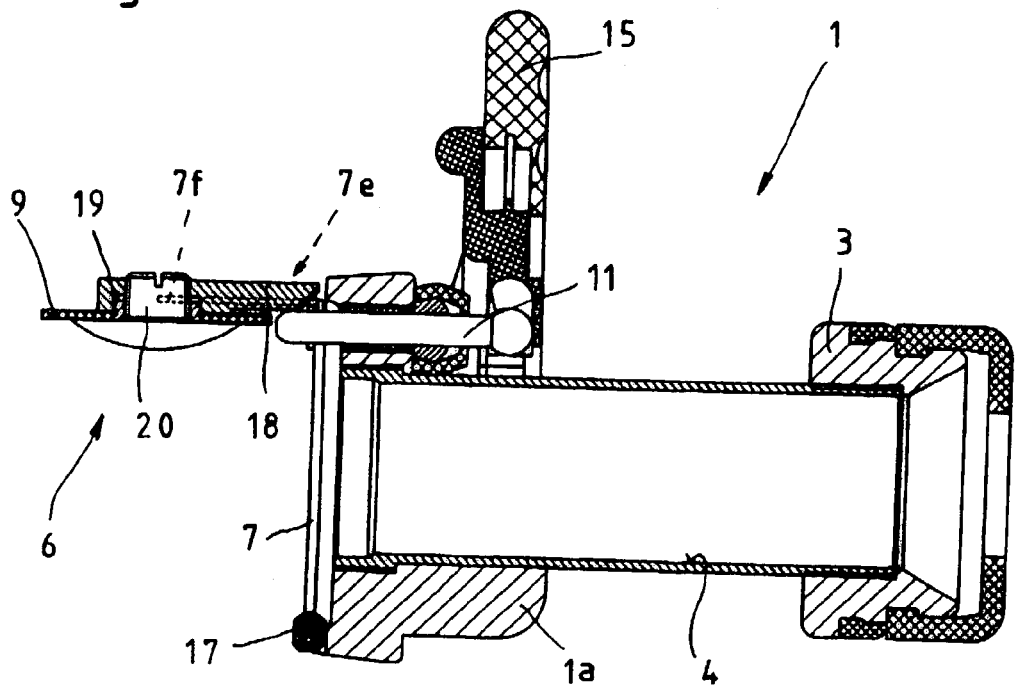

The structure and operating method of the valve body 6 can be seen in particular from cross-section illustrations in FIGS. 9b and 10b. These illustrations together with the perspective illustrations in FIGS. 9a and 10a show that in this embodiment the valve body 6, similarly as in the embodiment of FIG. 8, is activated by means of a lever 15 mounted on the housing 1a which drives a push rod 11.

Although the illustrated embodiments always foresee only one valve body 6 in order to close the instrument canal 4, is also possible of course to arrange several valve bodies 6 in the same plane of the instrument canal 5, each of which encloses the cross-section of the instrument canal 4 only partially and which are arranged in such a way that the valve bodies 6 overlap one another partly in the closed position and together close the cross-section of the instrument canal 4.

As an alternative to the illustrated embodiments, in which the connecting element 7 is configured each time as a single-strand spring wire, it is also possible of course to configure the connecting element 7 as a spring wire made of several intertwined strands. With this non-illustrated embodiment it is preferable if the individual strands of the connecting element 7 are connected to one another at individual spots by pressured or soldered points in order avoid too wide a spreading of the wire when the valve body 6 is rotated.

The illustrated construction of the valve body 6 is distinguished in that the valve body 6 is pre-tensioned in the closed direction by means of the connecting element 7 and thus a secure insulation of the instrument canal 4 is ensured. The simple construction of the mounting of the valve body 6 has the further advantage that it can thus be dismantled and assembled easily and quickly for cleaning and replacement purposes.

Reference Number Key

| | | | |
|---|---|---|---|
| 1 | Trocar head | 7f | Ends |
| 1a | Housing | 8 | Tube |
| 1b | Ring groove | 8a | Pressure spot |
| 1c | Ring groove segment | 9 | Insulating ring |
| 2 | Trocar sheath/additional component | 10 | Insulating rim |
| | | 11 | Push rod |
| 3 | Handle | 12 | Disk |
| 4 | Instrument canal | 13 | Spring |
| 5 | Trocar pin | 14 | Turning point |
| 6 | Valve body | 15 | Lever |
| 6a | Ring groove | 16 | Spring |
| 6b | Ring groove | 17 | Positioning element |
| 7 | Connecting element | 18 | Insulation mounting |
| 7a | Circle segment | 19 | Clamp segment |
| 7b | Segment | 20 | Bolt |
| 7c | Loop | | |
| 7d | Curvature | | |
| 7e | Segment | | |

What is claimed is:

1. Medical instrument comprising a housing, at least one valve body secured to the housing, a hollow instrument canal that is configured in the housing, the housing having an end wall with an outer surface, the outer surface of the end wall having an at least partially annular groove therein and an opening that can be closed by the valve body, which is pivotable into an open position by an instrument inserted into the instrument canal, and a bendable wire spring with an at least partially annular section corresponding to the at least partially annular groove in the outer surface of the end wall, wherein the annular section of the bendable wire spring is disposed in the corresponding annular groove in the outer surface of the end wall to secure the valve body to the housing, wherein the valve body is configured as a flap comprising non-bendable material mounted on the housing by the bendable wire spring so as to be pivotable and pre-tensioned in the closed direction.

2. Medical instrument according to claim 1, characterized in that the ring groove configured in the housing to secure the connecting element is designed as a surrounding ring groove.

3. Medical instrument according to claim 2, characterized in that the valve body has a ring groove, in particular a surrounding ring groove, for receiving the connecting element.

4. Medical instrument according to claim 3, characterized in that the valve body consists of at least two parts, which after their connection to one another, especially by clamping, bolting, or cementing, surround a corresponding segment of the connecting element.

5. Medical instrument according to claim 4, characterized in that the connecting element is constructed in the material of the valve body, in particular through casting.

6. Medical instrument according to claim 1, characterized in that the ring groove configured in the housing to secure the connecting element is designed as an interrupted ring groove.

7. Medical instrument according to claim 6, characterized in that at least one positioning element operating in conjunction with at least one ring groove segment is mounted on the connecting element.

8. The medical instrument according to claim 1, wherein the ring groove is positioned coaxially to the hollow instrument canal.

9. Medical instrument comprising a hollow instrument canal that is configured in a housing and can be closed by at least one valve body and rotated into open position by an instrument inserted into the instrument canal wherein the valve body is configured as a flap comprising non-bendable material mounted on the housing so as to be pivotable, by an elastic, bendable connecting element configured as a wire spring in such a way that the valve body is pre-tensioned in the closed direction, wherein the connecting element is secured on the housing and carries the valve body, and wherein the connecting element is secured in a surrounding ring groove configured in the housing and the valve body has a surrounding ring groove, for receiving the connecting element, characterized in that the portion of the connecting element that can be secured in the ring groove in the housing is surrounded by a tube of an inelastic material and the connecting element and the tube are pressure-joined together, wherein the valve body consists of at least two parts, which after their connection to one another surround a corresponding segment of the connecting element, and wherein the connecting element is constructed in the material of the valve body.

10. Medical instrument according to claim 9, characterized in that the connecting element and the tube are joined together through soldering, in particular laser soldering.

11. Medical instrument according to claim 10, characterized in that the outer diameter of the connecting element is only slightly smaller than the inner diameter of the tube.

12. Medical instrument according to claim 11, characterized in that the connecting element consists of spring steel or a super-elastic compound such as Ni—Ti, Cu—Al—Ni or Cu—Zn—Al alloys.

13. Medical instrument according to claim 12, characterized in that the valve body consists of hard plastic.

14. Medical instrument according to claim 13, characterized in that an insulating ring, in particular made of an elastomer plastic, can be secured on the valve body.

15. Medical instrument according to claim 14, characterized in that an insulating surface is configured on the housing coaxially surrounding the instrument canal to hold the insulating ring of the valve body.

16. Medical instrument according to claim 15, characterized in that the insulating surface is configured as a raised insulating rim, step, or level surface.

17. Medical instrument according to claim 16, characterized in that the valve body can, in addition, be mounted in the open position by means of a manually activatable mechanism.

18. Medical instrument according to claim 17, characterized in that the manually operable mechanism is configured as a push rod mounted eccentrically to the instrument canal, and this push rod can be pushed in the longitudinal direction of the instrument canal by means of an activating element stored on the housing.

19. Medical instrument according to claim 18, characterized in that the activating element is configured as a lever mounted so as to be rotatable on the housing.

20. Medical instrument according to claim 19, characterized in that the lever is pre-tensioned by means of a spring in the closed direction of the valve body.

21. Medical instrument according to claim 20, characterized in that the plane of the valve aperture is perpendicular to the longitudinal axis of the instrument canal.

22. Medical instrument according to claim 21, characterized in that an additional component can be secured on the housing in such a way that the additional component holds the ring groove or the ring groove segments, at least partially enclosing the connecting element in the ring groove or the ring groove segments.

23. Medical instrument according to claim 22, characterized in that the housing is a trocar head and the additional component is a trocar sheath of a trocar and can be secured on the trocar head.

24. Medical instrument according to claim 18, characterized in that the activating element is configured as a disk that can be pushed parallel to the instrument canal.

25. Medical instrument according to claim 24, characterized in that the disk is pre-tensioned by means of a spring in the closed position of the valve body.

26. Medical instrument according to claim 18, characterized in that the push rod is mounted parallel to the instrument canal.

27. Medical instrument according to claim 9, characterized in that the connecting element and the tube are pressure-squeezed together.

28. Medical instrument comprising a housing, at least one valve body comprising hard plastic secured to the housing, a hollow instrument canal that is configured in the housing, the housing having an end wall with an outer surface, the outer surface of the end wall having an at least partially annular groove therein and an opening that can be closed by the valve body, which is pivotable into an open position by an instrument inserted into the instrument canal, and a bendable wire spring with an at least partially annular section corresponding to the at least partially annular groove in the outer surface of the end wall, wherein the annular section of the bendable wire spring is disposed in the corresponding annular groove in the outer surface of the end wall to secure the valve body to the housing, wherein the valve body is configured as a flap comprising non-bendable material mounted on the housing by the bendable wire spring so as to be pivotable, and pre-tensioned in the closed direction.

* * * * *